United States Patent
Elghobashi

(10) Patent No.: US 11,607,337 B1
(45) Date of Patent: Mar. 21, 2023

(54) RECIRCULATING-AIR WARMING BLANKET

(71) Applicant: Said Elghobashi, Irvine, CA (US)

(72) Inventor: Said Elghobashi, Irvine, CA (US)

( * ) Notice: Subject to any disclaimer, the term of this patent is extended or adjusted under 35 U.S.C. 154(b) by 344 days.

(21) Appl. No.: 16/663,279

(22) Filed: Oct. 24, 2019

(51) Int. Cl.
  *A61F 7/00* (2006.01)

(52) U.S. Cl.
  CPC .......... *A61F 7/0097* (2013.01); *A61F 7/0085* (2013.01); *A61F 2007/006* (2013.01); *A61F 2007/0069* (2013.01); *A61F 2007/0091* (2013.01); *A61F 2007/0096* (2013.01)

(58) Field of Classification Search
  CPC .................. A61F 7/0097; A61F 7/0085; A61F 2007/0069; A61F 2007/0091; A61F 2007/0096
  See application file for complete search history.

(56) References Cited

U.S. PATENT DOCUMENTS

| | | | |
|---|---|---|---|
| 4,867,230 A | | 9/1989 | Voss |
| 5,125,238 A | | 6/1992 | Ragan |
| 5,304,217 A | | 4/1994 | Stephenson |
| 5,658,325 A | | 8/1997 | Augustine |
| 6,117,164 A | * | 9/2000 | Gildersleeve ............. A61F 7/02 607/108 |
| 6,126,393 A | | 10/2000 | Arnold |
| 6,331,695 B1 | | 12/2001 | West |
| 6,440,157 B1 | | 8/2002 | Shigezawa |
| 6,524,332 B1 | | 2/2003 | Augustine |
| 6,770,848 B2 | | 8/2004 | Haas |
| 7,517,360 B2 | | 4/2009 | Frey |
| 7,837,721 B2 | | 11/2010 | Augustine |
| 7,851,729 B2 | | 12/2010 | Augustine |
| 7,931,682 B2 | | 4/2011 | Albrecht |
| 7,976,572 B2 | | 7/2011 | Ziaimehr |
| 8,454,672 B2 | | 6/2013 | Van Duren |
| 9,510,971 B2 | | 12/2016 | Everadus |
| 9,687,093 B2 | | 6/2017 | Giles |
| 2010/0087901 A1 | * | 4/2010 | Hernandez ............. A61F 7/00 607/107 |

(Continued)

OTHER PUBLICATIONS

Suzuki A, Namba Y, Matsuura M, and Horisawa A, Airborne contamination in an operating suite: report of a five-year survey, J. Hyg., Camb. 1984, 93, 567-573.

(Continued)

*Primary Examiner* — Tigist S Demie

(57) ABSTRACT

A thermal device includes an inflatable non-perforated blanket, a conduit structure, and a recirculating assembly. The inflatable non-perforated blanket is configured to transport warm air internally. The conduit structure is configured to provide conduit to transport the warm air externally to the inflatable non-perforated blanket. The recirculating assembly is configured to inflate the inflatable non-perforated blanket with the warm air and: (1) to cause the warm air to flow from the first port to the second port in a first direction, and (2) to recirculate the warm air through the conduit structure to flow from the second port to the first port in the first direction. The inflatable non-perforated blanket includes first and second sheets. The first sheet faces ambient air and has a first thermal conductivity. The second sheet faces the subject body and has a second thermal conductivity higher than the first thermal conductivity.

28 Claims, 11 Drawing Sheets

(56) References Cited

U.S. PATENT DOCUMENTS

| | | | | |
|---|---|---|---|---|
| 2015/0173942 A1* | 6/2015 | Whitely | ............ | A61F 7/02 607/114 |
| 2018/0028702 A1* | 2/2018 | Lewis | ............ | A61F 7/0085 |

OTHER PUBLICATIONS

Moretti B, Larocca A, Napoli C, et al. Active warming systems to maintain perioperative normothermia in hip replacement surgery: a therapeutic aid or a vector of infection? J Hosp Infect. 2009;73(1):58-63.

Braeuer A and Quintel M, Forced-air warming: technology, physical background and practical aspects, Current Opinion in Anaesthesiology 2009, 22:769-774.

Brandt S, Oguz R, Huettner H, Waglechner G, Chiari A et al., Resistive-Polymer Versus Forced-Air Warming: Comparable Efficacy in Orthopedic Patients, International Anesthesia Research Society, 2010, 110:834-838.

Mcgovern P, Albrecht M, Belani K, et al. Forced-air warming and ultra-clean ventilation do not mix. J Bone Joint Surg Br. 2011;93(11):1537-1544.

Albrecht M, Gauthier R, Belani K, Litchy M, and Leaper D, Forced-air warming blowers: An evaluation of filtration adequacy and airborne contamination emissions in the operating room, American Journal of Infection Control May 2011, 321-328.doi:10.1016/j.ajic.2010.06.011.

Legg A, Cannon T, Hamer A. Do forced air patient-warming devices disrupt unidirectional downward airflow? J Bone Joint Surg Br. 2012;94(2):254-256.

Belani K, Albrecht M,Mcgovern P, Reed M, and Nachtsheim, C. Patient Warming Excess Heat: The Effects on Orthopedic Operating Room Ventilation Performance, International Anesthesia Research Society, Apr. 2012, 1:6, DOI: 10.1213/ANE.0b013e31825f81e2.

Desari KB, Albrecht M, Harper M. Effect of forced-air warming on the performance of operating theatre laminar flow ventilation. Anesthesia. 2012;67(3):244 249.

Legg A and Hamer A. Forced-air patient warming blankets disrupt unidirectional airflow, Bone Joint J 2013;95-B:407-410.

Wood A , Moss C, Keenan A, Reed M, and Leaper D. Infection control hazards associated with the use of forced-air warming in operating theatres, Journal of Hospital Infection, Jul. 2014, 1-9. http://dx.doi.org/10.1016/j.jhin.2014.07.010.

He X, Karra S, Pakseresht K, Apte S, and Elghobashi S, Effect of heated-air blanket on the dispersion of squames in an operating room, Int. J. Numerical Methods in Biomedical Engineering, 2018; 1-24, https://doi.org/10.1002/cnm.2960.

Jain S and Reed M, Laminar Air Flow Handling Systems in the Operating Room, Surgical Infections, vol. 20, No. 2, 2019:1-8.

Kumin M, Harper C, Reed M, Bremner S, Perry N, and Scarborough M, Reducing Implant Infection in Orthopaedics (RIIiO): a pilot study for a randomised controlled trial comparing the influence of forced air versus resistive fabric warming technologies on postoperative infection rates following orthopaedic implant surgery in adults,2019, PMCID: PMC6245696, 1-24, https://www.ncbi.nlm.nih.gov/pmc/articles/PMC6245696/.

"Bair Hugger patient warming System" Brochure—5 pages: https://www.3m.com/3M/en_US/company-us/all-3m-products/~/AII-3M-Products/Health-Care/Medical/Surgical-Safety-Solutions/Patient-Warming-Blankets/?N=5002385+8707795+8707798+8711017+8711100+8711119+3294857497&rt=r3.

"Hot Dog Warming System"; Product catalogue; Published 2012 by Augustine Temperature Management; 2 pages. https://hotdogwarming.com/.

Kanmed Warmcloud Brochure (2 pages) : https://kanmed.se/products/warmcloud/.

Mistral-Air Forced Air Warming Blankets by Stryker Brochure (3 pages) https://www.stryker.com/us/en/acute-care/products/mistral-air.html.

* cited by examiner

RECIRCULATING-AIR WARMING BLANKET

BACKGROUND

Technical Field

One disclosed aspect of the embodiments relates to a warming device. In particular, an embodiment is related to a perioperative recirculating-air warming blanket.

Description of the Related Art

Perioperative care is the medical care for patients before, during, and after surgery. It is usually provided to patients in hospitals, surgical centers, medical facilities, or doctors' offices. The care includes a period, called a perioperative period, during which the patient is prepared by health care professionals (e.g., hospital staff, nurses, physician assistants) in various aspects prior to, during, or after the surgery. These aspects may be physical, emotional, or psychological.

Hypothermia, defined as the state where the patient's core temperature falls below 36° C., may be beneficial and detrimental. The potential benefits may include protection against the deleterious effects of cerebral ischemia and malignant hyperthermia. The detrimental effects may include increased susceptibility to perioperative wound infection by causing impaired immunity. Other adverse effects of hypothermia include shivering, lowered resistance to infection, and prolonged duration of drug action. To reduce these adverse effects, several techniques or devices to warm the patient have been developed with various degrees of success. These include cotton blankets, warm fluid infusion, and forced air warming.

In forced air warming techniques, warming blankets or devices have been available for several years. U.S. Pat. No. 6,524,332 issued to Augustine et al. discloses a thermal blanket with tubes having a large number of apertures with varying hole density. One disadvantage of this technique is the release of warm air outside the blanket, which generates plumes that enhance turbulent mixing and dispersion of squames in the operating room (OR). The squames may reach the wound location, leading to increased probability of infection. A study conducted by X. He, S. Karra. P. Pakseresht, S. V. Apte, and S. Elghobashi ("Effect of heated-air blanket on the dispersion of squames in an operating room," Int. J. Numer Meth Biomed Engen. 2018; e2960. https://doi.org/10.1002/cnm.2960) indicates that the hot air from the blower in these devices and the resultant plumes are capable of lifting the particles and transporting them to the side tables, above the operating table, and the surgical site. U.S. Pat. No. 8,772,676 issued to Augustine et al. discloses a heating blanket. The disadvantages of this technique include the complex post-use care and non-disposability. Other devices or techniques suffer disadvantages such as high power consumption, non-disposability, required support of patient's body weight when used as a mattress.

SUMMARY

One disclosed aspect of the embodiments is directed to a thermal device that provides warm air to a disposable warming blanket with low power consumption and uniform temperature distribution.

A thermal device includes an inflatable non-perforated blanket, a conduit structure, and a recirculating assembly. The inflatable non-perforated blanket has first and second ports at first and second regions, respectively, and is configured to transport warm air internally. The conduit structure is configured to provide conduit to transport the warm air externally to the inflatable non-perforated blanket. The recirculating assembly is configured to inflate the inflatable non-perforated blanket with the warm air and: (1) to cause the warm air to flow from the first port to the second port in a first direction through the first and second regions of the inflatable non-perforated blanket, and (2) to recirculate the warm air through the conduit structure to flow from the second port to the first port in the first direction externally to the inflatable non-perforated blanket. The inflatable non-perforated blanket is adapted to fit a subject body and includes first and second sheets forming first and second groups of tubes arranged longitudinally. The first sheet faces ambient air and has a first thermal conductivity. The second sheet faces the subject body and has a second thermal conductivity higher than the first thermal conductivity.

Further features of the disclosure will become apparent from the following description of exemplary embodiments with reference to the attached drawings.

DESCRIPTION OF THE EMBODIMENTS

Figure 1:
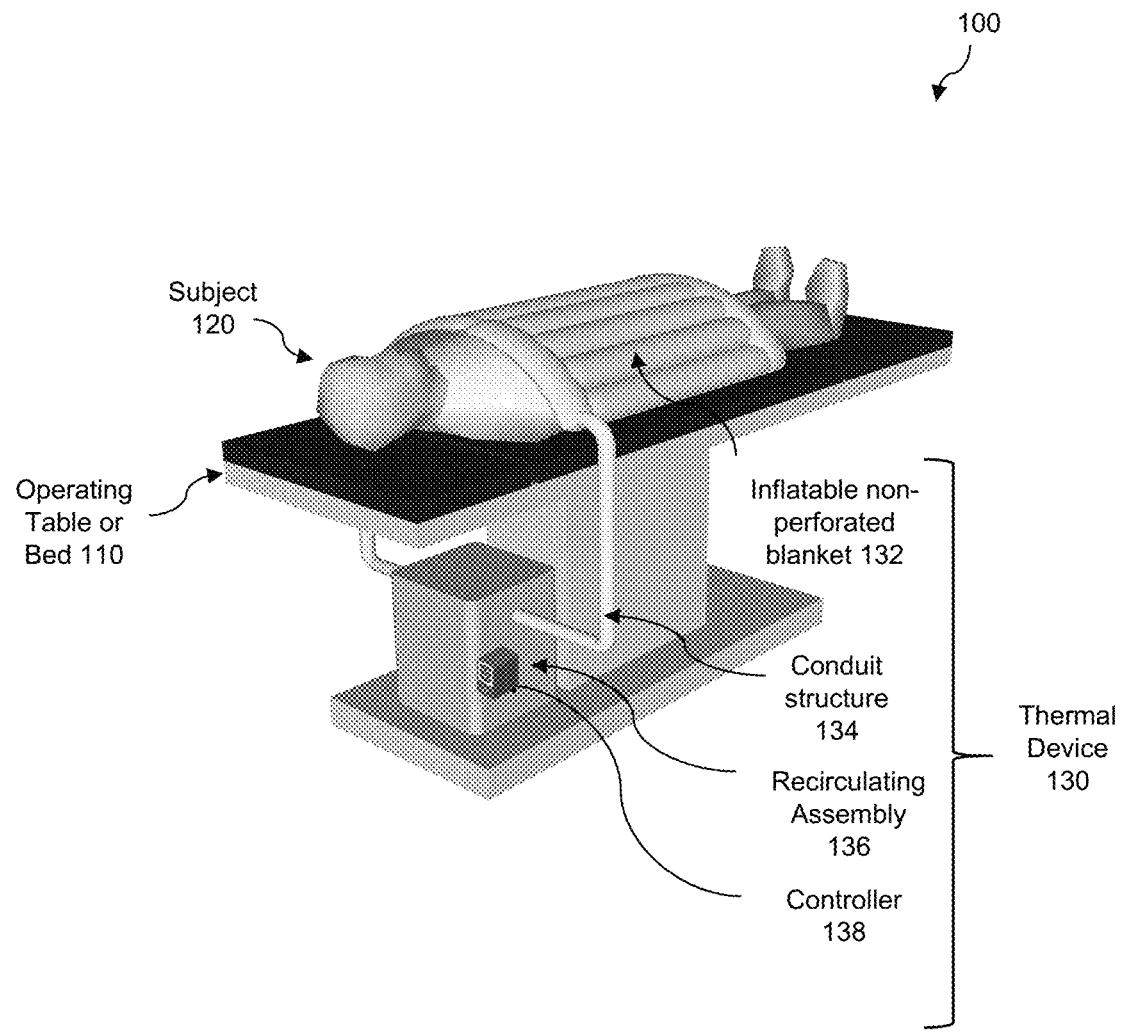
FIG. 1 is a diagram illustrating a system in a typical perioperative environment.

A description is given of several embodiments. In each embodiment, an example is described where the disclosure is applied to a perioperative recirculating thermal device.

A thermal device is an apparatus that includes an inflatable non-perforated blanket, a conduit structure, and a recirculating assembly. The inflatable non-perforated blanket has first and second ports at first and second regions, respectively, and is configured to transport warm air internally. The conduit structure is configured to provide conduit to transport the warm air externally to the inflatable non-perforated blanket. The recirculating assembly is configured to inflate the inflatable non-perforated blanket with the warm air and: (1) to cause the warm air stream to flow from the first port to the second port in a first direction through the first and second regions of the inflatable non-perforated blanket, and (2) to recirculate the warm air stream through the conduit structure to flow from the second port to the first port in the first direction externally to the inflatable non-perforated blanket.

The thermal device further includes a controller to control flow of the warm air stream. This may be performed by sending control signals to various air valves located inside the conduits in the conduit structure. The valves are opened or closed to direct the air stream to flow in a predetermined direction.

The recirculating assembly includes a heater to generate the warm air by heating the air and a blower to blow the warm air to the inflatable non-perforated blanket. The recirculating assembly may further include at least an environmental sensor which may be any one of a temperature sensor, a pressure sensor, and a flow sensor. There may be multiple environmental sensors populated around the recirculating assembly or any other suitable locations. In one embodiment, the controller controls the flow based on a measurement obtained from the environmental sensor.

The conduit structure includes an inlet valve to control flow from the ambient air. In one embodiment, it further includes an inflow conduit to transport the warm air to the first port, an outflow conduit to transport the warm air from the second port to a recirculating port, and a recirculating conduit to transport the warm air from the recirculating port to the recirculating assembly. The recirculating conduit has a recirculating valve to control flow of the warm air. Each of the inflow and outflow conduits is a flexible hose.

In one embodiment, the controller opens the inlet valve to draw the ambient air to the recirculating assembly and closes the recirculating valve in an initialization period. It closes the inlet valve to stop drawing the ambient air to the recirculating assembly after the initial period and opens the recirculating valve to draw the warm air from the outflow conduit, through the recirculating conduit and to the recirculating assembly.

The conduit structure is reconfigurable by the controller to reverse flow of the warm air stream from the first direction to a second direction opposite to the first direction. The second direction is from the second port to the first port when the warm air stream flows through the inflatable non-perforated blanket and is from the first port to the second port when the warm air flows externally to the inflatable non-perforated blanket.

The inflatable non-perforated blanket may have a variety of shapes to accommodate the subject or the patient body, such as the upper body, the lower body, the entire body, or any part of the body.

The conduit structure may be reconfigurable by the controller in a cycle based on at least one of a time parameter and an environmental parameter from the measurement obtained from the environmental sensor.

FIG. 1 is a diagram illustrating a system 100 in a typical perioperative environment. The system 100 includes an operating table or bed 110, a subject 120, and a recirculating thermal device 130. The system 100 may include more or less than the above elements.

The operating table or bed 110 is a means on which the subject 120 lies during a perioperative period. This may be before the surgery (preoperative), during surgery (intraoperative), or after surgery (postoperative). In some embodiments, the operating table or bed 110 may be any suitable means for the subject 120 to rest on regardless of his or her surgical condition. The subject 120 is a patient who is undergoing a surgery or who is in need of being warmed due to his or her health conditions. The recirculating thermal device 130 provides warmth to the subject 120 using a forced air warming technique. Typically, a medical staff (e.g., a nurse) puts the inflatable blanket 132 on the subject 120 such that the inflatable blanket 132 covers the subject 120 in a body area or region that needs warming. For example, the inflatable blanket 132 may cover the front side of the upper part of the body of the subject 120.

Depending on the condition of the subject 120, the inflatable blanket 132 may cover the subject 120 directly with direct contact, or through a layer such as a garment, hospital gown, or a sheet. The inflatable blanket 132 is made of flexible material that can fit the body of the subject 120. In addition, the inflatable blanket 132 may be covered by another layer such as a regular blanket or a bed sheet.

The thermal device 130 includes an inflatable non-perforated blanket 132, a conduit structure 134, a recirculating assembly 136, and a controller 138. For clarity, these components are shown separately. In particular, the inflatable non-perforated blanket 132 may be manufactured to be separate from the other components so that it can be disposed of when necessary. In one embodiment, more than one component may be integrated into a single component, or a component may be split to occupy in more than one other component. For example, the controller 138 and the recirculating assembly 136 may be integrated into a single component.

The inflatable non-perforated blanket 132 is a flexible structure that is non-perforated and completely sealed so that the warm air cannot leak out to the ambient air. This is to avoid contamination or infection to the patient as discussed above. The blanket 132 contains a number of tubular ducts or tubes that are initially collapsed to become flat. When warm air is blown into these tubes, the tubes are inflated to a predetermined size or under a predetermined pressure or temperature. Since the lower surface of the blanket 132 is made of high thermal conductivity material and is in contact with the body of the subject 120, the tubes act as a heat source that allows the thermal energy in the warm air to be transferred to the body of the subject 120.

The conduit structure 134 is configured to provide conduit to transport the warm air externally to the inflatable non-perforated blanket 132. The conduit structure 134 is attached to the blanket 132 and the recirculating assembly 136 to provide a recirculating air path for the warm air, when exiting the blanket 132 at the exit end, to return to the blanket 132 at the entrance end. The conduit structure 134 may be configured to transport the warm air in one fixed direction. In another embodiment, it may be reconfigured to transport the warm air in a first direction for some time period and then transport the warm air in a second direction opposite of the first direction. In this reconfigurable mode, the process may be repeated or cycled as long as necessary to maintain balance in thermal distribution over the surface of the blanket 132 or to reduce the thermal or mechanical stress on the blanket 132.

The recirculating assembly 136 performs two basic functions: blowing the warm air through the blanket 132 and heating the air to a predetermined temperature and maintaining the air temperature at that predetermined temperature. It pumps the warm air through the blanket 132, inflates the tubes in the blanket 132, and causes the warm air to flow through the blanket 132 and to recirculate through the conduit structure 134. The warm air, therefore, forms a continuous loop of flow of air stream that circulates through the blanket 132. The heat from the warm air stream circulating through the blanket 132 is transferred to the body of the subject 120 during the air flow through the blanket 132.

Figure 2:
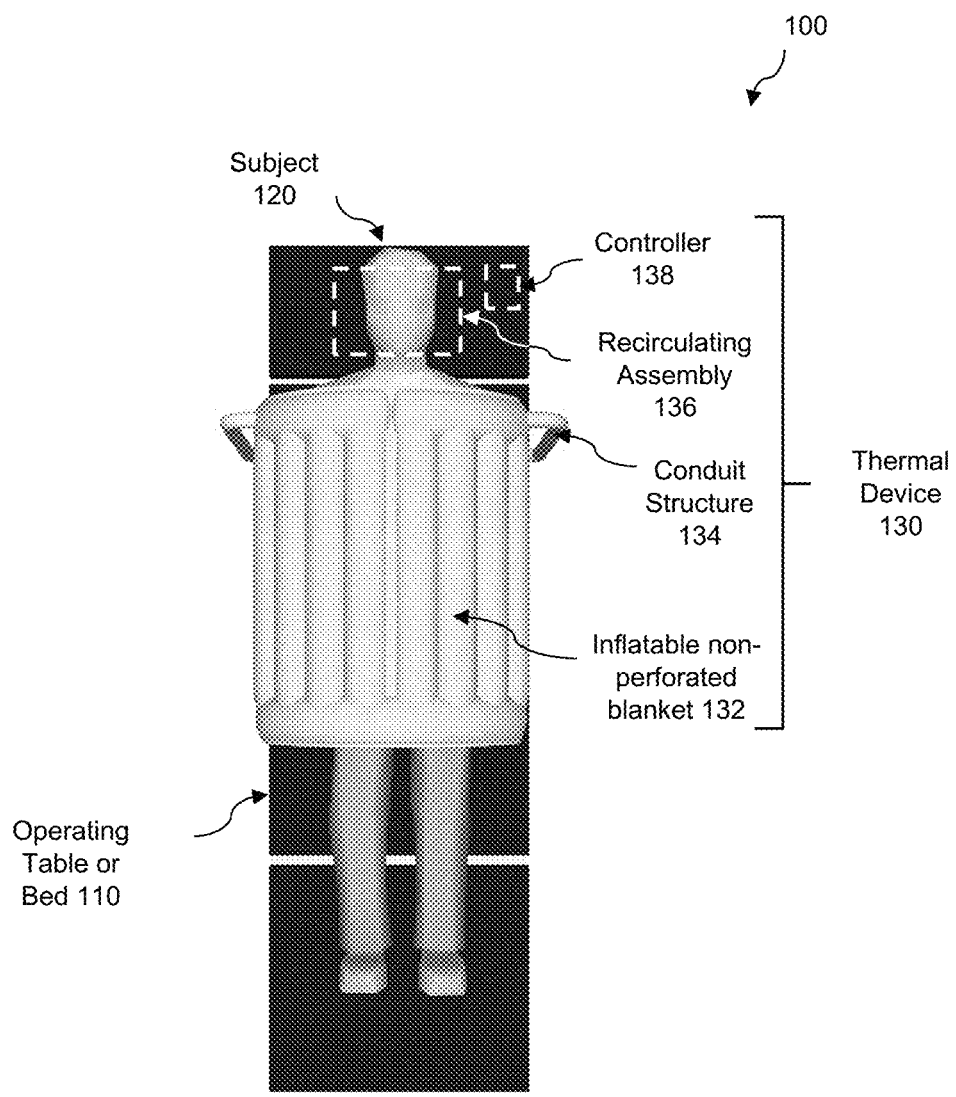
FIG. 2 is a diagram illustrating the system in a top view.

FIG. 2 is a diagram illustrating the system 100 in a top view. As in FIG. 1, the system 100 includes an operating table or bed 110, a subject 120, and a thermal device 130. As in FIG. 1, the thermal device 130 includes an inflatable non-perforated blanket 132, a conduit structure 134, a recirculating assembly 136, and a controller 138. From the top down, it is seen that the inflatable non-perforated blanket 132 covers the upper part of the body of the subject 120. The recirculating assembly 136 and the controller 138 are shown to be located under the operating table or bed 110 for illustrative purposes. They can be located or positioned at any suitable location.

Figure 3:
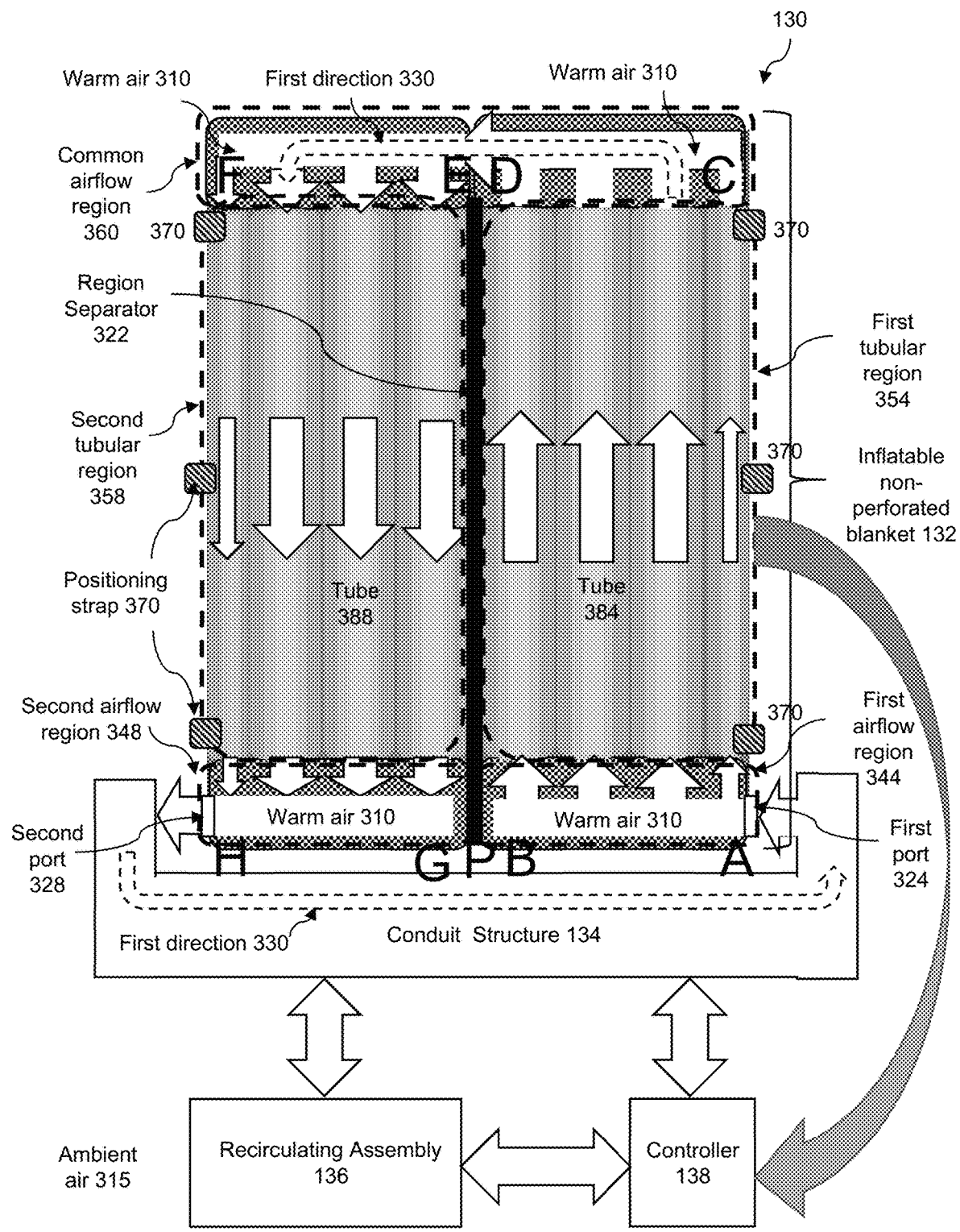
FIG. 3 is a diagram illustrating a recirculating thermal device.

FIG. 3 is a diagram illustrating a thermal device 130 with a detailed description of its components. As in FIGS. 1 and 2, the thermal device 130 includes the inflatable non-perforated blanket 132, the conduit structure 134, the recirculating assembly 136, and the controller 138. FIG. 3 shows the details of the inflatable non-perforated blanket 132 and the interactions of these components. These components are typically separated from one another. Therefore, the thermal device 130 is easy to maintain and highly portable. In addition, the inflatable non-perforated blanket 132 is separate from the other components and therefore it is disposable when necessary. Since the inflatable non-perforated blanket 132 is typically used on patients more often than the other components, it may be susceptible to wear-out. Accordingly, the disposability is a benefit that allows the thermal device 130 to be used for longer periods. The inflatable non-perforated blanket 132 may have a number of positioning straps 370 to secure the blanket to desired locations over the subject or patient body 120. The positioning straps 370 may be made by any suitable materials such as plastic with any convenient fastening mechanism such as adhesive.

The inflatable non-perforated blanket 132 has first and second ports 324 and 328 at first and second airflow regions 344 and 348, respectively. The first and second ports 324 and 328 provide the mechanical interface to allow the conduit structure 134 to be connected, coupled, attached, clamped, fastened, or joined to the blanket 132. The inflatable non-perforated blanket 132 is configured to transport warm air 310 internally. The first port 324 provides the connection to the conduit structure 134 at one end for the warm air 310 to flow into the blanket 132 (in a first direction 330), or to flow out of the blanket 132 in a second direction 930 (shown in FIGS. 9 and 11) opposite of the first direction 330. The second port 328 provides the connection to the conduit structure 134 at another end for the warm air 310 to flow out of the blanket 132 (in a first direction 330), or to flow into the blanket 132 in a second direction 930 (shown in FIGS. 9 and 11) opposite of the first direction 330.

The first and second airflow regions 344 and 348 are in contact with first and second tubular regions 354 and 358, respectively. The first and second tubular regions 354 and 358 include several tubular ducts or tubes 384 and 388, respectively, arranged longitudinally or along the length of the blanket 132.

Both the first and second tubular regions 354 and 358 are in contact with a common airflow region 360 at the distal end. The first air flow region 344 and the first tubular regions 354 are separated from (i.e., not in contact with) the second air flow region 348 and the second tubular regions 358 by a region separator 322. The region separator 322 prevents the warm air flowing through the first airflow regions 344 and the first tubular region 354 from leaking into the second airflow regions 348 and the second tubular region 358, and vice versa.

The warm air 310 flows through the inflatable non-perforated blanket 132 in the first direction 330 due to the blowing force of the electric blower in the recirculating assembly 136. The first direction 330 traverses the inflatable non-perforated blanket 132 from the first port 324 at point A to point B at the end of the first airflow region 344. The warm air 310 then flows into the multiple tubes 384. The tubes 384 transport the warm air from the first airflow region 344 (marked by points A and B) to the common airflow region 360 (marked by points C and D). In the common airflow region 360, there is no region separator. Therefore, the warm air stream 310 can flow freely from the region marked CD to the region marked EF. Then, the warm air stream 310 continues flowing through the second tubular region 358. Specifically, the warm air stream 310 flows through the tubes 388 from the common air flow region 360 (marked by points E and F) to the second air flow region 348 (marked by points G and H). The region separator 322 prevents the warm air stream 310 from leaking or permeating to the first tubular region 354. The warm air stream 310 then exits the inflatable non-perforated blanket 132 through the second port 328 and enters the conduit structure 134 to recirculate back to the first port 324.

As discussed above, the conduit structure 134 is configured to provide conduit to transport the warm air stream externally to the blanket 132. The recirculating assembly is configured to inflate the inflatable non-perforated blanket with the warm air and: (1) to cause the warm air stream 310 to flow from the first port 324 to the second port 328 in the first direction 330 through the first and second tubular regions 354 and 358 of the blanket 132, and (2) to recirculate the warm air stream 310 through the conduit structure 134 to flow from the second port 328 to the first port 324 in the first direction 330 externally to the inflatable non-perforated blanket 132.

Figure 4:
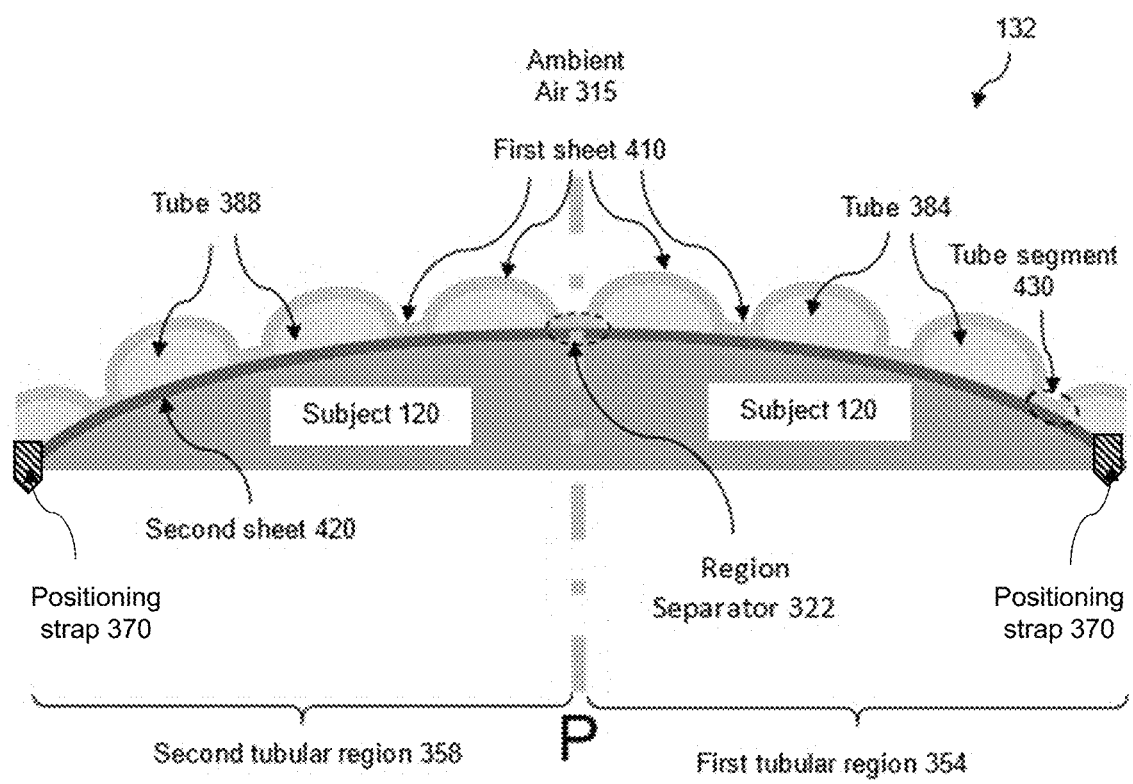
FIG. 4 is a diagram illustrating an inflatable non-perforated blanket in a section view.

FIG. 4 is a diagram illustrating the inflatable non-perforated blanket 132 in a section view. The inflatable non-perforated blanket 132 is adapted to fit the body of the subject 120. It may be attached or tightened to the subject 120 in any suitable manner, such as using the provided self-adhesive plastic straps 370. It includes a first sheet 410 and a second sheet 420. The first and second sheets 410 and 420 are made of stretchable or flexible material such as plastic.

The first sheet 410 faces the ambient air or the external area and has a first thermal conductivity which is very low (to act as an insulator). The second sheet 420 faces the body of the subject 120 and has a second thermal conductivity. The second thermal conductivity is much higher than the first thermal conductivity such that uniformity of temperature distribution when the warm air flows over the surface of the second sheet is maintained.

In one embodiment, the first sheet 410 may be made of Polyvinyl chloride (PVC) which has a thermal conductivity coefficient of about 0.19 W/m K (Watts per meter-Kelvin), or epoxy which has a thermal conductivity coefficient of about 0.17 W/m K, or any other suitable material. The second sheet 420 may be made of any suitable material that is sufficiently flexible. For example, the second sheet 420 may be made of Polyethylene low density (PEL) which has a thermal conductivity coefficient of about 0.33 W/m K, or Polyethylene high density (PEH) which has a thermal conductivity coefficient of about 0.5 W/m K. It may also be possible to use advanced plastic materials that have much higher thermal conductivity coefficients, for example, in the order of 100 W/m K, to make the second sheet 420.

The second sheet 420 is stretchable to accommodate the shape of the subject 120. The first sheet 410 forms a layer on the second sheet 420 and is press-sealed to the second sheet 420 at several tube segments 430. The tube segments 430 are spaced at approximately equal distances across the width of the blanket 132 to define the tubes 384 and 388. Initially the sheet 410 is flat and the tubes 384 and 388 are in a deflated state. When air is pumped into the blanket 132, the warm air stream 310 inflates the tubes 384 and 388 as it travels along the length of the blanket 132.

The first sheet 410 is also press-sealed at the region separator 322 so that it acts as a barrier to prevent the warm air stream 310 from leaking or penetrating between the first and second tubular regions 354 and 358. The region separator 322 stops at the common air flow region 360 to allow the warm air 310 to flow from the first tubular regions 354 to the second tubular regions 358 in the first direction 330 or from the second tubular regions 358 to the first tubular regions 354 in the second direction 930 (in FIG. 9).

Figure 5:
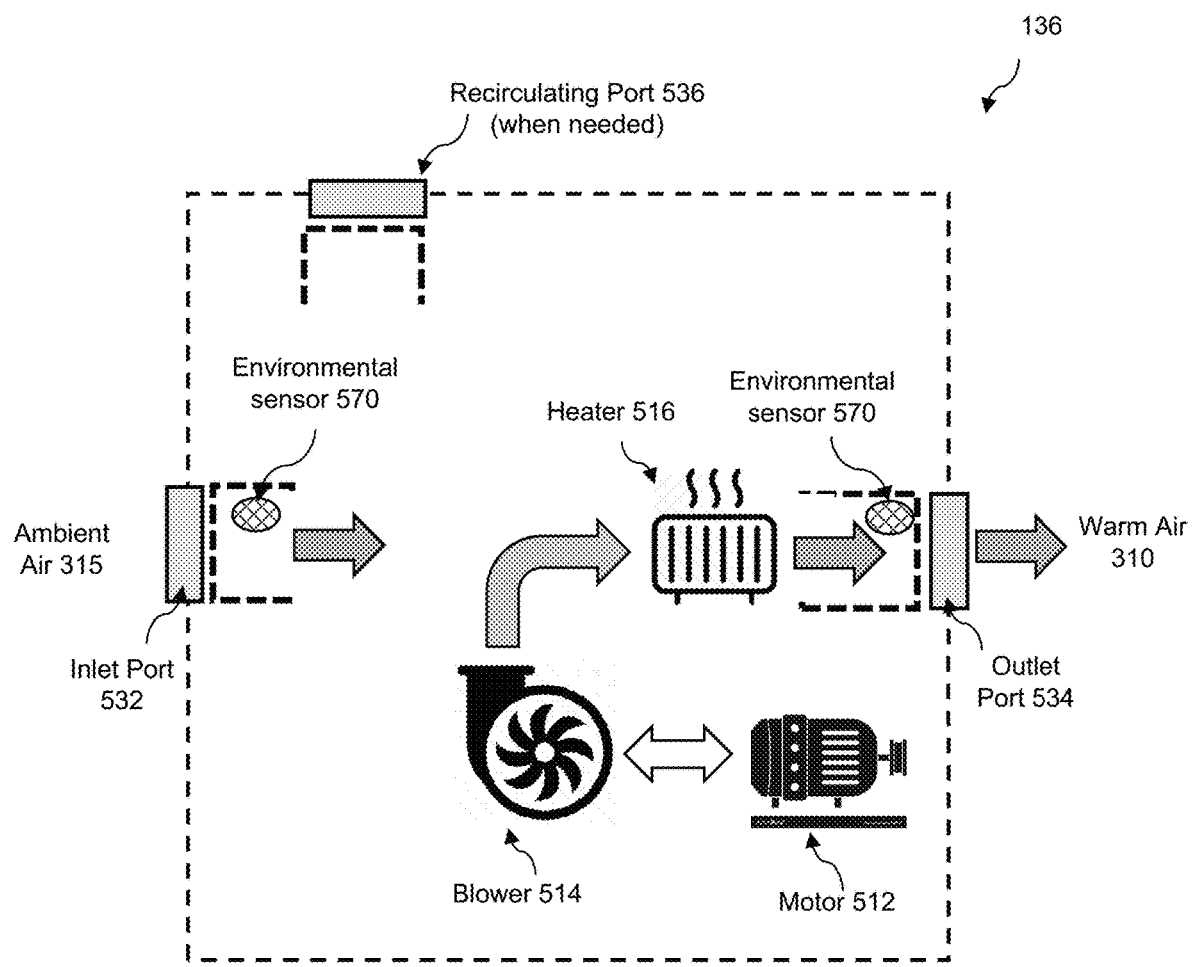
FIG. 5 is a diagram illustrating a recirculating assembly.

FIG. 5 is a diagram illustrating the recirculating assembly 136. The recirculating assembly 136 is configured to generate the warm air stream 310 that inflates the inflatable non-perforated blanket 132. The force provided by the recirculating assembly 136 causes the warm air to flow through the blanket 132 internally and to recirculate through the conduit structure 134 externally to the blanket 132. The recirculating assembly 136 includes a motor 512, a blower 514, and a heater 516. It has an inlet port 532 that receives the ambient air 315 during the initialization period. It has an outlet port 534 to deliver the warm air stream 310 to the blanket 132 through the conduit structure 134. In some embodiments, it also has a recirculating port 536 to provide connection to the recirculating air stream in a reconfigurable mode.

The motor 512 provides power to the blower 514. It may be an electric motor that drives the blower 514 with a shaft. The blower 514 blows the air and creates a force that pushes or propels the air forward toward the outlet port 534. The blower 514 may be any suitable blower. It may include a propeller or several fan blades arranged with a wheel in an appropriate structural assembly. The blade and wheel mechanism may be any suitable configuration, such as shrouded radial blade, open radial blade, open paddle wheel, backward inclined, backward curved, airfoil blade, forward curved multi-vane (squirrel cage), and backward curved radial.

The heater 516 may employ any suitable heating mechanism, such as resistive heating. The heater 516 may be remotely controlled by the controller. Once activated, it generates heat to warm the air stream blown by the blower 514. One particular advantage of an embodiment of the recirculating thermal device 130 is the efficient energy utilization. Since the warm air recirculates through the blanket 132, any amount of heat that is not fully transferred to the subject 120 continues to flow through the recirculating assembly 136. Accordingly, except during the initialization period, the heater 516 does not heat fresh cool air from the ambient air 315. Instead, it heats an air stream that has been heated before. Accordingly, the heater 516 does not need to provide a full heating power as in the initialization period. It needs only to provide enough heat to maintain the temperature of the warm air stream at a predetermined level. The environmental sensors 570 located in the recirculating assembly 136 or other locations include one or more temperature sensors that provide readings of the air stream temperature. Based on these readings, which may be obtained remotely, the controller 138 generates control signal to the heater 516 to adjust the power accordingly.

The arrangement of the motor 512, the blower 514, and the heater 516 may follow any configuration that provides an efficient power utilization and noise suppression. For example, the blower 514 may be positioned to blow the air toward the motor 512 and the heater 516 to provide a cooling mechanism for the motor 513. Alternatively, the motor 512 may be positioned outside the air stream to provide more air propulsion efficiency.

Figure 6:
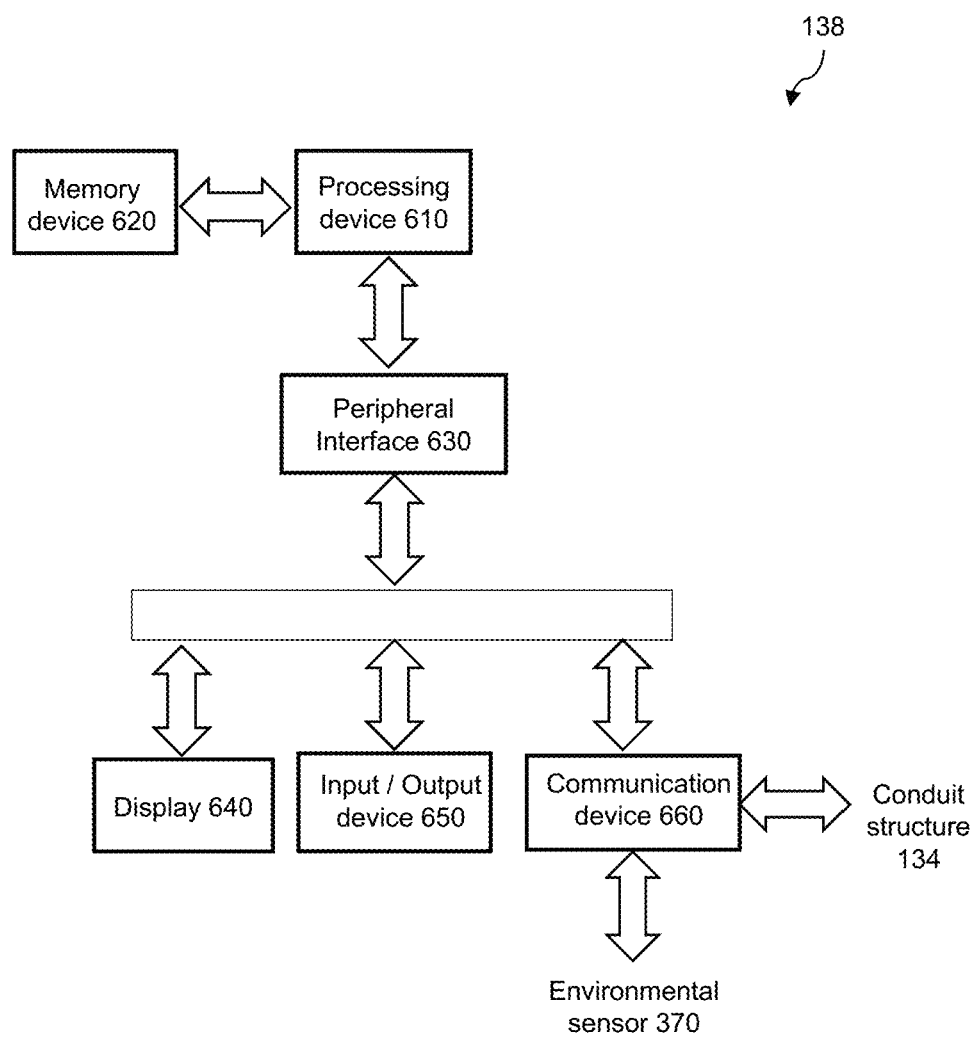
FIG. 6 is a diagram illustrating a controller.

FIG. 6 is a diagram illustrating the controller 138. The controller 138 is configured to control the flow of the warm air stream 310. The controller 138 includes a processing device 610, a peripheral interface 630, a memory device 620, a display 640, an I/O device 650, and a communication device 660. These components may be located in a housing or scattered at several locations. The controller 138 may include more or less components than the above. In addition, some components may be integrated into a single component or split into more components. Furthermore, not all components are located or positioned within the same housing. For example, the I/O device 650 (e.g., keyboard) may be located outside the housing of the controller 138 to allow a user to enter control parameters or other information. Similarly, the display 640 may be located outside the housing to allow a user to read the status of the thermal device.

The processing device, processor, or circuit 610 is a programmable device that may execute a program or a collection of instructions to carry out a task. It may be a central processing unit (CPU), a general-purpose processor, a digital signal processor, a microcontroller, or a specially designed processor such as one design from Applications Specific Integrated Circuit (ASIC).

The peripheral interface 630 in a highly integrated chipset that includes many functionalities to provide interface to several devices such as memory devices, input/output devices, storage devices, network devices, etc. The memory device 620 may be any appropriate memory devices such as random access memory (RAM), read-only memory (ROM), cache memory, and flash memory. The memory device 620 may store instructions or programs, loaded from a mass storage device (e.g., a memory stick), that, when executed by the processing device 610, cause the processing device 610 to perform operations as described elsewhere, such as flow control. It may also store data used in the operations, including the control parameters, the predetermined levels or thresholds. The ROM may include instructions, programs, constants, or data that are maintained whether it is powered or not. The flash memory may store programs, instructions, constants, tables, coefficients. It may be erased and programmed as necessary.

The display 640 may include a display device such as liquid crystal display (LCD), light-emitting diode (LED), etc. The display may provide the status of the thermal device, sensor readings, and other user interface functionalities. The I/O device or controller 650 controls input devices (e.g., stylus, keyboard, mouse, microphone, sensors) and output devices (e.g., display, audio devices, speaker, scanner, printer). The communication device 660 provides interface to a network and/or a wireless controller. The communication device 660 transmits and receives information or data packets to and from a wired, wireless network (nor shown). It may receive readings from the environmental sensors 570. It may also issue commands or control signals to the conduit structure 134, such as activating or deactivate the air valves. The network may be a local area network (LAN), an intranet, an extranet, or the Internet.

The conduit structure:

The thermal device 130 may operate in one or more operational modes. These modes include a fixed mode and a reconfigurable mode. In the fixed mode, the thermal device 130 operates with a simple structure and configuration where the direction of the air stream is fixed, for example, the first direction 330. In the reconfigurable mode, the thermal device 130 operates with a complex structure and configuration where the direction of the air stream is changed between the first direction 330 and the second direction 930. The component that plays the main role in the mode configuration is the conduit structure 134.

Figure 7:
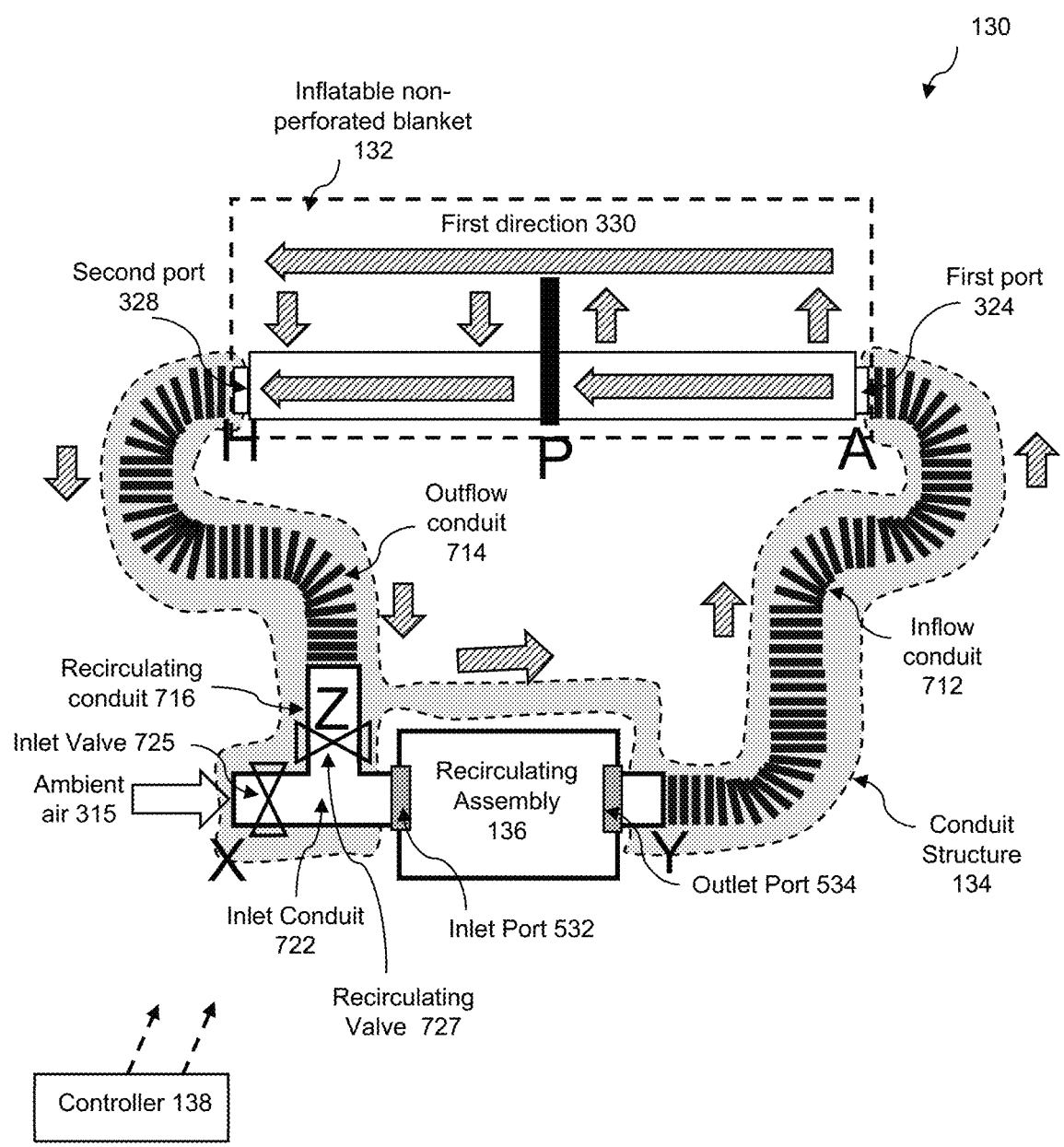
FIG. 7 is a diagram illustrating a conduit structure.

FIG. 7 is a diagram illustrating the thermal device 130 using the conduit structure 134 in a fixed mode. The conduit structure 134 includes the components outside the blanket 132 and the recirculating assembly 136. It is shown in shaded area in the diagram. The conduit structure 134 in the fixed mode includes an inflow conduit 712, an outflow conduit 714, a recirculating conduit 716, an inlet valve 725 and a recirculating valve 727.

The inflow conduit 712 connects the recirculating assembly 136 to the blanket 132 at the first port 324. It may be any suitable conduit such as a flexible or corrugated hose or tube. It transports the warm air stream 310 from the recirculating assembly 136 to the blanket 132. The outflow conduit 714 connects the blanket 132 to the recirculating assembly 136 at the second port 328. It may be any suitable conduit such as a flexible or corrugated hose or tube. It transports the warm air stream 310 from the blanket 132 to the recirculating assembly 136 to the blanket 132 via the recirculating conduit 714. The recirculating conduit 714 provides a path for the warm air stream 310 to recirculate. The inlet valve 725 controls the flow of the air stream from the ambient air 315 to the recirculating assembly 136. The recirculating valve 727 is located in the recirculating conduit 716 to control the flow of the air stream from the blanket 132 to the recirculating assembly 136. In one embodiment, the inlet valve 725 and/or the recirculating valve 727 operates in an on-off mode where the valve is open to allow the air stream to pass through or is closed to inhibit the air stream to pass through. The mechanism to activate the opening or closure of the valve may be performed by wired or wireless controls.

The operation of the conduit structure 134 is under the control of the controller 138. In essence, the controller 138 receives the environmental readings from one or more environmental sensors 570 and activates or deactivates the valves 725 and 727 according to these readings. In addition, the controller 138 may perform operations independently of the environmental readings such as based on a timer or user's inputs.

In a typical scenario, the thermal device in the fixed mode has two operational periods: an initialization period and an operational period. In the initialization period, the recirculating assembly 136 draws the ambient air 315 and blows the heated air to inflate the tubes 384 and 388 inside the blanket 132 and propels the warm air through these tubes. The environmental sensor 570, such as a pressure sensor, monitors the air pressure at the inlet port 532 or outlet port 534, or the inflow and/or outflow conduits 712 and 714. It continuously transmits the measured parameter to the controller 138 either through wired or wireless connections. When this pressure reaches a predetermined level, the thermal device 130 switches to the operational period. In the operational period, the thermal device 130 stops drawing the ambient air 315 and allows the warm air to recirculate.

The operation of the thermal device 130 may be carried out as follows. In the initialization period, the controller 138 closes the recirculating valve 727 and opens the inlet valve 725 to draw the ambient air 315 to the recirculating assembly 136. From the ambient air 315, it generates the warm air stream 310. The warm air stream 310 flows from point Y at the outlet port 534 through the inflow conduit 712 to the first port 324 at point A, and enters the blanket 132. The warm air stream 310 continues to flow in the first directions 330 to the common air flow region 360 and to the second port 328 at point H. The warm air stream 310 then exits the blanket 132 and flows through the outflow conduit 714. Since the recirculating conduit 716 is closed at point Z, the warm air stream 310 cannot exit, allowing the air pressure inside the blanket 132 to build up. Eventually, the air pressure inside the blanket 132 reaches a predetermined level, which indicates that the tubes 384 and 388 have been sufficiently inflated. At that point, the controller 138 sends the control signals to close the inlet valve 725 and to open the recirculating valve 727 and the thermal device 130 enters the operational period.

In the operational period, the recirculating assembly 136 stops drawing the ambient air 315 to the recirculating assembly 136 and draws the warm air stream 310 from the outflow conduit 714 through the recirculating conduit 716 and to the inlet port 532 of the recirculating assembly 136. The warm air stream 310 continuously recirculates in a closed loop that flows through the blanket 132 and the recirculating assembly 136.

Figure 8:
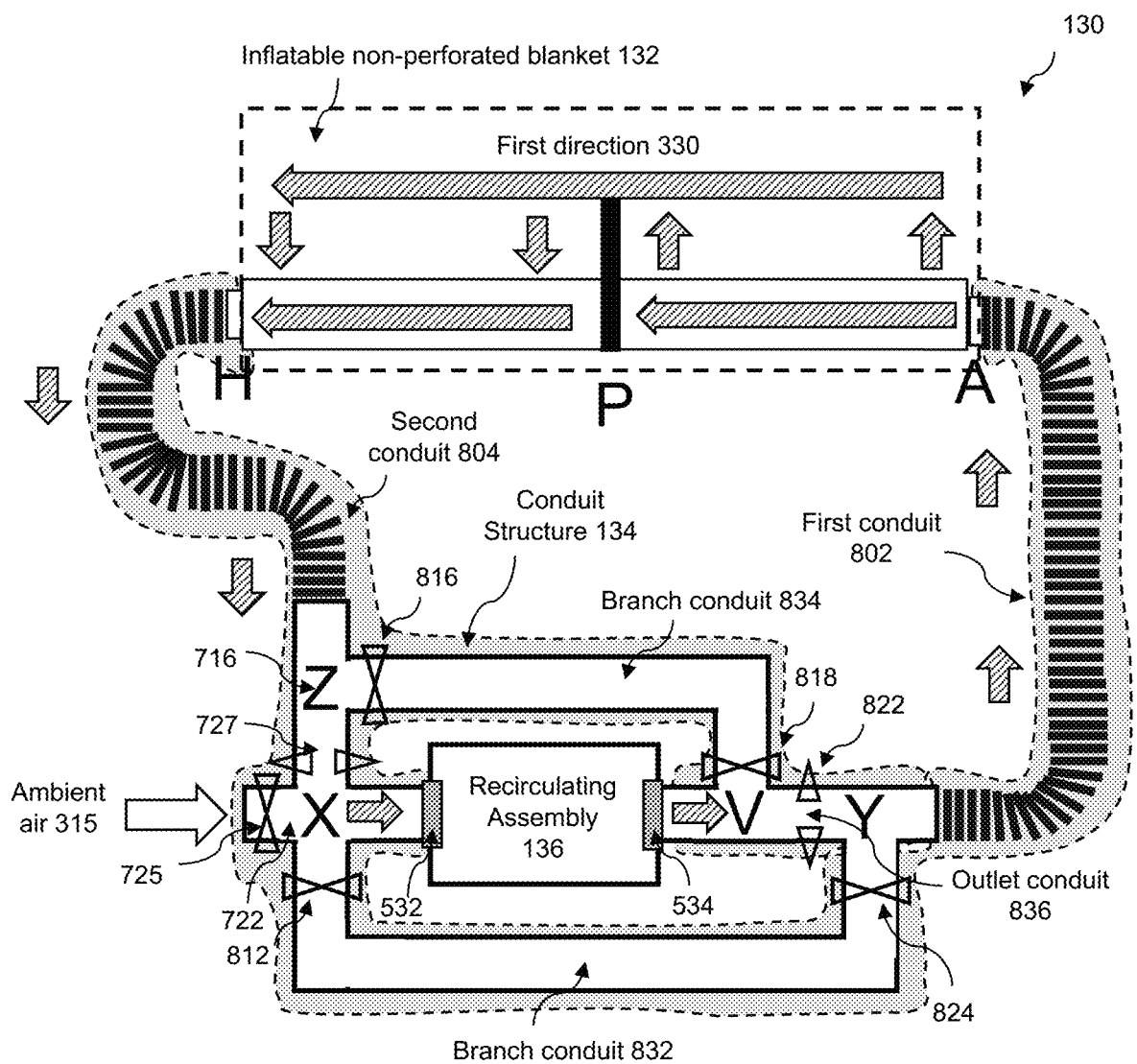
FIG. 8 is a diagram illustrating a first embodiment of a reconfigurable conduit structure operating in a first direction.
Figure 9:
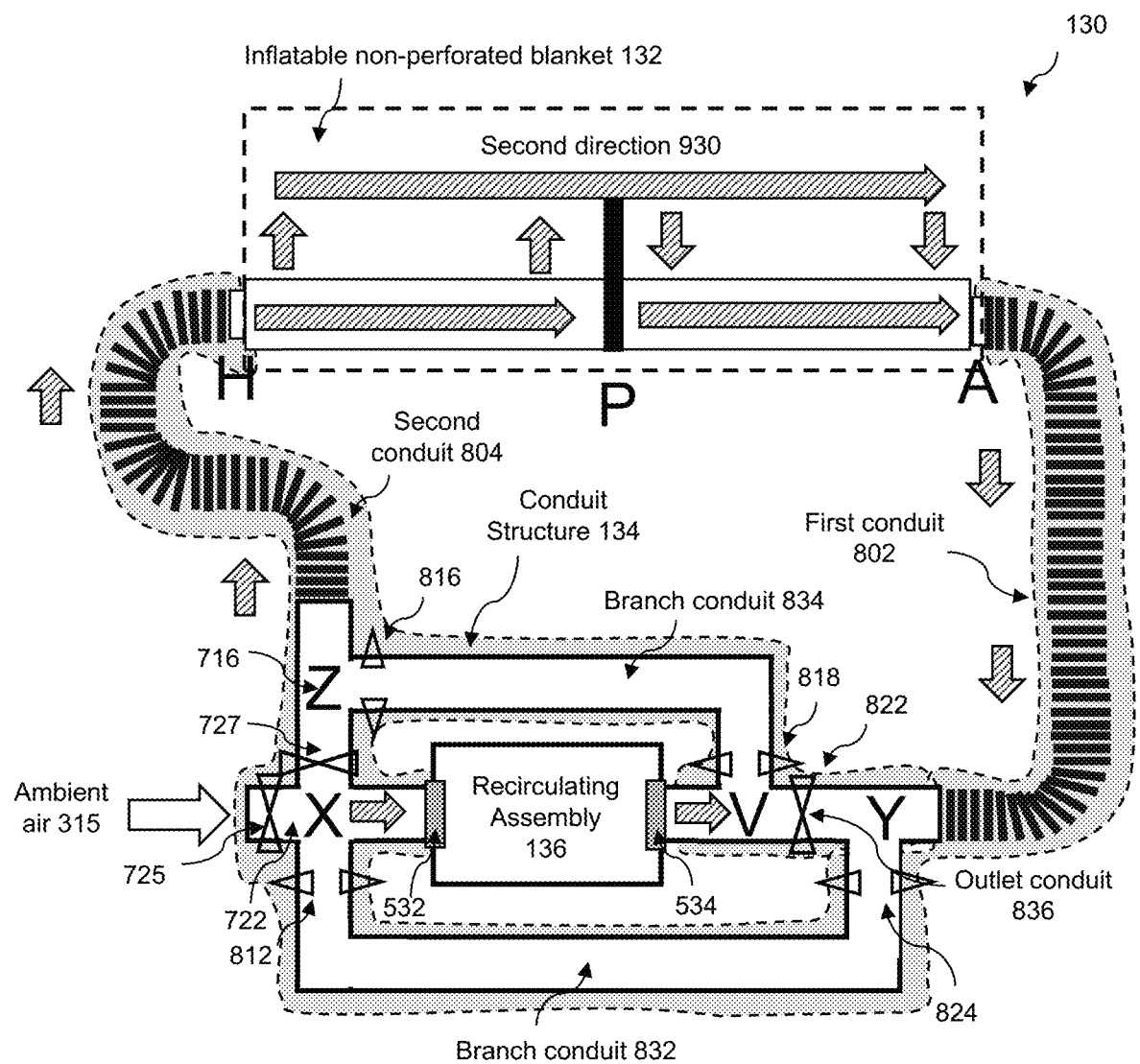
FIG. 9 is a diagram illustrating a first embodiment of a reconfigurable conduit structure operating in a second direction.
Figure 10:
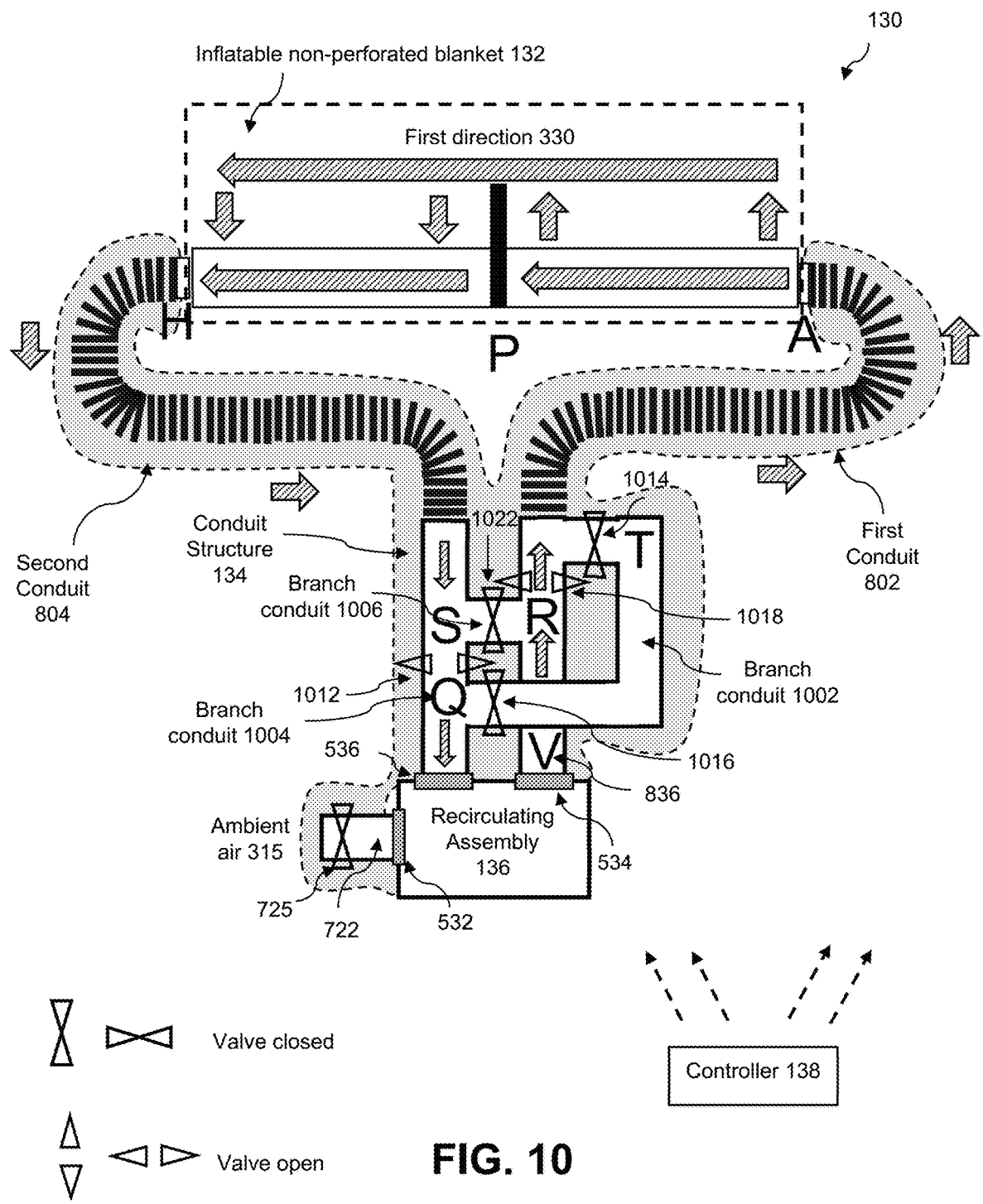
FIG. 10 is a diagram illustrating a second embodiment of a reconfigurable conduit structure operating in a first direction.
Figure 11:
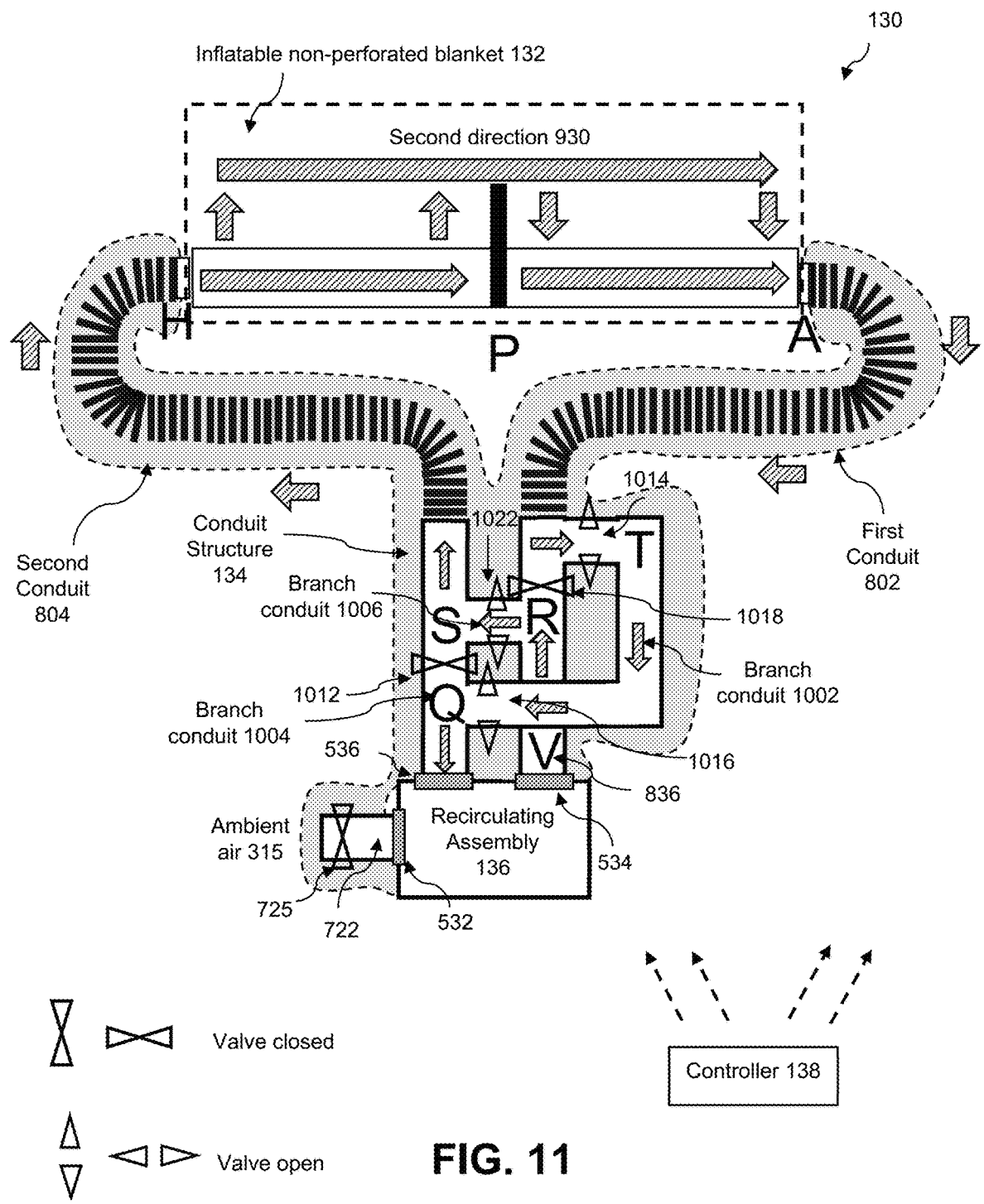
FIG. 11 is a diagram illustrating a second embodiment of a reconfigurable conduit structure operating in a second direction.

The conduit structure 134 may be designed to be reconfigurable so that the flow direction of the warm air stream may be reversed and cycled back and forth in any desired time period. By cycling the warm air stream in two opposite directions, the thermal device 130 reduces the thermal and/or mechanical stress on the surface of the sheets of the blanket 132 and accommodates any irregularities of the shape of the subject 120 to balance the thermal distribution. Two embodiments illustrate this reconfigurable mode. FIGS. 8 and 9 show the first embodiment. FIGS. 10 and 11 show the second embodiment.

FIG. 8 is a diagram illustrating the thermal device 130 using a first embodiment of a reconfigurable conduit structure 134 operating in a first direction. The inflow conduit 712 is replaced by a first conduit 802 and the outflow conduit 714 is replaced by a second conduit 804 to reflect the bidirectional nature of these conduits. In addition to the recirculating conduit 716 and the inlet conduit 722 shown in FIG. 7, the conduit structure 134 has an outlet conduit 836 and two branch conduits 832 and 834. It has several air valves to change the air stream direction. For illustration, six valves are shown. The inlet valve 725 is located at the inlet conduit 722 to draw the ambient air 315 and the recirculating valve 727 is located at the recirculating conduit 722 to provide conduit for the recirculating air stream as before. The outlet conduit 836 has a valve 822. The branch conduit 832 has a valve 812 located near the inlet conduit 722 and a valve 824 located near the outlet conduit 836. Depending on the size of the branch conduit 832, the two valves 812 and 824 may be merged into a single valve. The branch conduit 834 has a valve 816 near the recirculating conduit 714 and a valve 818 near the outlet conduit 836. Depending on the size of the branch conduit 834, the two valves 816 and 818 may be merged into a single valve.

In the initial period, the controller 138 controls the valves as follows: closes the valves 727, 812, 824, 816, and 818; and opens the valves 725 and 822. The ambient air 315 is drawn into the recirculating assembly 136 through the inlet conduit 722. The warm air stream 310 exits the recirculating assembly 136 and is propelled to enter the blanket 132 through the first conduit 802. The warm air stream 310 exits the blanket 132 and flows through the second conduit 804. Since the valves 727 and 816 are closed the warm air stream 310 accumulates at point Z to build up pressure. When the internal pressure reaches a predetermined level, the initialization period is completed and the thermal device 130 switches to the operational period. This is performed by the controller 138 to control the valves by issuing control signals to open or close the valves accordingly.

In the operational period, the thermal device 130 can direct the warm air stream 310 in two directions. FIG. 8 illustrates the first direction 330 and FIG. 9 illustrates the second direction 930. As discussed earlier, the first direction 330 goes from the first port 324 (point A in FIG. 7) to the second port 328 (point H), then from point H to points Z and X, then through the recirculating assembly 136 to points V and Y, and returns to point A. The controller 138 issues control signals to the valves to direct the warm air stream to flow in the first direction 330 as follows: closes the valves 725, 812, 824, 816, 818; and opens the valves 727 and 822.

FIG. 9 is a diagram illustrating the thermal device 130 using a first embodiment of a reconfigurable conduit structure 134 operating in a second direction. FIG. 9 only illustrates the operational mode. The initialization mode is the same as in FIG. 8. The second direction is shown as the arrow 930. The second direction 930 goes from the inlet port 532 (point X) through the recirculating assembly 136 to points V; then from point V to point Z; then through the second conduit 804 to the second port 328 (point H); then through the blanket 132 to the first port 324 (point A); then through the first conduit 802 to point Y; and then from point Y to point X and continues through the recirculating assembly 136.

The controller 138 issues control signals to the valves to direct the warm air stream to flow in the second direction 930 as follows: closes the valves 725, 727, and 822; and opens the valves 816, 818, 812, and 824.

FIG. 10 is a diagram illustrating the thermal device 130 using a second embodiment of a reconfigurable conduit structure 134 operating in a first direction. The conduit structure 130 has the first and second conduits 802 and 804 as in FIG. 8. It has three conduits: the outlet conduit 836 and three branch conduits 1002, 1004, and 1006. It has six valves. The inlet valve 725 is located at the inlet conduit 722 as before. The outlet conduit 836 has a valve 1018. The branch conduit 1002 has valves 1014 and 1016. Depending on the size of the conduit 1002, the valves 1014 and 1016 may be merged into a single valve. The branch conduit 1004 has a valve 1012. The branch conduit 1016 has a valve 1022.

In the initial period, the controller 138 controls the valves as follows: closes the valves 1012, 1014, 1016, and 1022; and opens the valves 725 and 1018. The ambient air 315 is drawn into the recirculating assembly 136 through the inlet conduit 722. The warm air stream 310 exits the recirculating assembly 136 and is propelled to enter the blanket 132 through the outlet conduit 836 and the first conduit 802. The warm air stream 310 exits the blanket 132 and flows through the second conduit 804. Since the valves 1012 and 1022 are closed, the air stream 310 accumulates at valve 1012 to build up pressure. When the internal pressure reaches a predetermined level, the initialization period is completed and the thermal device 130 switches to the operational period. As before, this is performed by the controller 138 to control the valves.

In the operational period, the thermal device 130 can direct the warm air stream 310 in two directions. FIG. 10 illustrates the first direction 330 and FIG. 11 illustrates the second direction 930. The first direction 330 goes from the first port 324 (point A) to the second port 328 (point H), then from point H to points S and Q near valve 1012, then through the recirculating assembly 136 to point V and then to point R near valve 1018, and returns to point A. The controller 138 issues control signals to the valves to direct the warm air stream 310 to flow in the first direction 330 as follows: closes the valves 725, 1014, 1016, and 1022; and opens the valves 1012 and 1018.

FIG. 11 is a diagram illustrating the thermal device 130 using a second embodiment of a reconfigurable conduit structure 134 operating in a second direction. FIG. 11 only illustrates the operational mode. The initialization mode is the same as in FIG. 10. The second direction is shown as the arrow 930. The second direction 930 goes from the outlet port 534 (point V) to point R and turns to point S; then from point S through the second conduit 804 to the second port 328 (point H); through the blanket 132 to the first port 324 (point A); then through the first conduit 802 to point T; and then from point T to point Q and continues through the recirculating assembly 132.

The controller 138 issues control signals to the valves to direct the warm air stream to flow in the second direction 930 as follows: closes the valves 725, 1012, and 1018; and opens the valves 1014, 1016, and 1022.

Variations of the above configurations may be carried out. For example, additional conduits or valves may be included to provide more flexibility in directing the warm air stream.

Elements of one embodiment may be implemented by hardware, firmware, software or any combination thereof. The term hardware generally refers to an element having a physical structure such as electronic, electromagnetic, optical, electro-optical, mechanical, electro-mechanical parts, etc. A hardware implementation may include analog or digital circuits, devices, processors, applications specific integrated circuits (ASICs), programmable logic devices (PLDs), field programmable gate arrays (FPGAs), or any electronic devices. The term software generally refers to a logical structure, a method, a procedure, a program, a routine, a process, an algorithm, a formula, a function, an expression, etc. The term firmware generally refers to a logical structure, a method, a procedure, a program, a routine, a process, an algorithm, a formula, a function, an expression, etc., that is implemented or embodied in a hardware structure (e.g., flash memory, ROM, EROM). Examples of firmware may include microcode, writable control store, micro-programmed structure.

When implemented in software or firmware, the elements of an embodiment may be the code segments to perform the necessary tasks. The software/firmware may include the actual code to carry out the operations described in one embodiment, or code that emulates or simulates the operations. The program or code segments may be stored in a processor or machine accessible medium. The "processor readable or accessible medium" or "machine readable or accessible medium" may include any non-transitory medium that may store information. Examples of the processor readable or machine accessible medium that may store include a storage medium, an electronic circuit, a semiconductor memory device, a read only memory (ROM), a flash memory, an erasable programmable ROM (EPROM), a floppy diskette, a compact disk (CD) ROM, an optical disk, a hard disk, etc. The machine accessible medium may be embodied in an article of manufacture. The machine accessible medium may include information or data that, when accessed by a machine, cause the machine to perform the operations or actions described above. The machine accessible medium may also include program code, instruction or instructions embedded therein. The program code may include machine readable code, instruction or instructions to perform the operations or actions described above. The term "information" or "data" here refers to any type of information that is encoded for machine-readable purposes. Therefore, it may include program, code, data, file, etc.

All or part of an embodiment may be implemented by various means depending on applications according to particular features, functions. These means may include hardware, software, or firmware, or any combination thereof. A hardware, software, or firmware element may have several modules coupled to one another. A hardware module is coupled to another module by mechanical, electrical, optical, electromagnetic or any physical connections. A software module is coupled to another module by a function, procedure, method, subprogram, or subroutine call, a jump, a link, a parameter, variable, and argument passing, a function return, etc. A software module is coupled to another module to receive variables, parameters, arguments, pointers, etc. and/or to generate or pass results, updated variables, pointers, etc. A firmware module is coupled to another module by any combination of hardware and software coupling methods above. A hardware, software, or firmware module may be coupled to any one of another hardware, software, or firmware module. A module may also be a software driver or interface to interact with the operating system running on the platform. A module may also be a hardware driver to configure, set up, initialize, send and receive data to and from a hardware device. An apparatus may include any combination of hardware, software, and firmware modules.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus comprising:
an inflatable non-perforated blanket having first and second ports at first and second regions, respectively, and configured to transport warm air internally;
a conduit structure configured to provide conduit to transport the warm air externally to the inflatable non-perforated blanket; and
a recirculating assembly configured to inflate the inflatable non-perforated blanket with the warm air and: (1) to cause the warm air to flow from the first port to the second port in a first direction internally to the inflatable non-perforated blanket through the first and second regions, and (2) to recirculate the warm air through the conduit structure to flow from the second port to the first port in the first direction externally to the inflatable non-perforated blanket;
wherein the inflatable non-perforated blanket is adapted to fit a subject body and includes first and second sheets forming first and second groups of tubes arranged longitudinally,
wherein the first sheet faces ambient air and is made of a first material having a first thermal conductivity,
wherein the second sheet faces the subject body and is made of a second material different from the first material and having a second thermal conductivity higher than the first thermal conductivity, and
wherein a ratio between the second thermal conductivity and the first thermal conductivity is greater than or equal to 500.

2. The apparatus of claim 1 wherein the second thermal conductivity is higher than the first thermal conductivity such that uniformity of temperature distribution over surface of the second sheet is maintained.

3. The apparatus of claim 1 further comprising a controller to control flow of the warm air.

4. The apparatus of claim 3 wherein the recirculating assembly comprises:
a heater to generate the warm air by heating; and
a blower to blow the warm air to the inflatable non-perforated blanket.

5. The apparatus of claim 3 wherein the conduit structure comprises an inlet valve at an inlet port to control flow from the ambient air.

6. The apparatus of claim 5 wherein the conduit structure further comprises:
an inflow conduit to transport the warm air to the first port; and
an outflow conduit to transport the warm air from the second port to a recirculating port; and
a recirculating conduit to transport the warm air from the recirculating port to the recirculating assembly,
wherein the recirculating conduit has a recirculating valve to control flow of the warm air.

7. The apparatus of claim 6 wherein one of the inflow and outflow conduits is a flexible hose.

8. The apparatus of claim 6 wherein the controller:
opens the inlet valve to draw the ambient air to the recirculating assembly and closes the recirculating valve in an initial period; and
closes the inlet valve to stop drawing the ambient air to the recirculating assembly after the initial period and opens the recirculating valve to draw the warm air from the outflow conduit, through the recirculating conduit and to the recirculating assembly.

9. The apparatus of claim 6 wherein the recirculating assembly includes an environmental sensor being one of a temperature sensor, a pressure sensor, and a flow sensor.

10. The apparatus of claim 9 wherein the controller controls the flow based on a measurement obtained from the environmental sensor.

11. The apparatus of claim 10 wherein the conduit structure is reconfigurable by the controller in a cycle based on at least one of a time parameter and an environmental parameter from the measurement obtained from the environmental sensor.

12. The apparatus of claim 5 wherein the conduit structure is reconfigurable by the controller to reverse flow of the warm air from the first direction to a second direction opposite to the first direction,
wherein the second direction is from the second port to the first port when the warm air flows through the inflatable non-perforated blanket and is from the first port to the second port when the warm air flows externally to the inflatable non-perforated blanket.

13. The apparatus of claim 1 wherein the first material is made of Polyvinyl chloride (PVC) or epoxy.

14. The apparatus of claim 1 wherein the first thermal conductivity is 0.19 W/mK or higher.

15. The apparatus of claim 1 wherein the second thermal conductivity is between 100 W/mK to 200 W/mK.

16. The apparatus of claim 1 wherein the second layer is in contact with the subject body directly or through a layer.

17. A method comprising:
transporting warm air in an inflatable non-perforated blanket having first and second ports from the first port to the second port;

providing conduit to transport the warm air in a conduit structure externally to the inflatable non-perforated blanket;

inflating the inflatable non-perforated blanket with the warm air via a recirculating assembly;

causing the warm air to flow from the first port to the second port in a first direction internally to the inflatable non-perforated blanket through the first and second regions, via the recirculating assembly; and recirculating the warm air through the conduit structure to flow from the second port to the first port in the first direction externally to the inflatable non-perforated blanket, via the recirculating assembly;

wherein the inflatable non-perforated blanket is adapted to fit a subject body and includes first and second sheets forming first and second groups of tubes arranged longitudinally, wherein the first sheet faces ambient air and is made of a first material having a first thermal conductivity, wherein the second sheet faces the subject body and is made of a second material different from the first material and having a second thermal conductivity higher than the first thermal conductivity, and wherein a ratio between the second thermal conductivity and the first thermal conductivity is greater than or equal to 500.

18. The method of claim 17 wherein the second thermal conductivity is higher than the first thermal conductivity such that uniformity of temperature distribution over surface of the second sheet is maintained.

19. The method of claim 17 further comprising controlling flow of the warm air.

20. The method of claim 19 wherein recirculating comprises:

generating the warm air by heating; and blowing the warm air to the inflatable non-perforated blanket.

21. The method of claim 19 wherein providing conduit comprises controlling flow from the ambient air via an inlet valve.

22. The method of claim 21 wherein recirculating comprises:

transporting the warm air to the first port in an inflow conduit;

transporting the warm air from the second port to a recirculating port in an outflow conduit; and transporting the warm air from the recirculating port to the recirculating assembly in a recirculating conduit, wherein the recirculating conduit has a recirculating valve to control flow of the warm air.

23. The method of claim 22 wherein controlling flow of the warm air comprises:

opening the inlet valve to draw the ambient air to the recirculating assembly and closing the recirculating valve in an initial period; and closing the inlet valve to stop drawing the ambient air to the recirculating assembly after the initial period and opening the recirculating valve to draw the warm air from the outflow conduit, through the recirculating conduit and to the recirculating assembly.

24. The method of claim 21 wherein providing conduit comprises reconfiguring to reverse flow of the warm air from the first direction to a second direction opposite to the first direction, wherein the second direction is from the second port to the first port when the warm air flows through the inflatable non-perforated blanket and is from the first port to the second port when the warm air flows externally to the inflatable non-perforated blanket.

25. The method of claim 17 wherein the first material is made of Polyvinyl chloride (PVC) or epoxy.

26. The method of claim 17 wherein the first thermal conductivity is 0.19 W/mK or higher.

27. The method of claim 17 wherein the second thermal conductivity is between 100 W/mK to 200 W/mK.

28. The method of claim 17 wherein the second layer is in contact with the subject body directly or through a layer.

* * * * *